US012138030B2

United States Patent
Hyde et al.

(10) Patent No.: US 12,138,030 B2
(45) Date of Patent: *Nov. 12, 2024

(54) SYSTEM AND METHODS FOR MICRO IMPULSE RADAR DETECTION OF PHYSIOLOGICAL INFORMATION

(71) Applicant: Deep Science, LLC, Bellevue, WA (US)

(72) Inventors: Roderick A. Hyde, Redmond, WA (US); David William Wine, Seattle, WA (US); Brian C. Holloway, Snoqualmie, WA (US)

(73) Assignee: Deep Science, LLC, Bellevue, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/330,165

(22) Filed: Jun. 6, 2023

(65) Prior Publication Data

US 2023/0309846 A1 Oct. 5, 2023

Related U.S. Application Data

(63) Continuation of application No. 16/657,688, filed on Oct. 18, 2019, now Pat. No. 11,701,020.
(Continued)

(51) Int. Cl.
*A61B 5/0507* (2021.01)
*A61B 5/00* (2006.01)
(Continued)

(52) U.S. Cl.
CPC .......... *A61B 5/0507* (2013.01); *A61B 5/0205* (2013.01); *A61B 5/0285* (2013.01);
(Continued)

(58) Field of Classification Search
CPC ....... A61B 5/0522; A61B 5/0205; A61B 5/05; A61B 5/053; A61B 5/0816; A61B 5/0507
See application file for complete search history.

(56) References Cited

U.S. PATENT DOCUMENTS 1,903,823 A 4/1993 Lougheed
5,573,012 A 11/1996 McEwan
(Continued)

FOREIGN PATENT DOCUMENTS

EP 2012139 A1 1/2009
FR 1053332 A 2/1954
(Continued)

OTHER PUBLICATIONS

Paulson, C. N., Chang, J. T., Romero, C. E., Watson, J., Pearce, F. J., & Levin, N. (Nov. 2005). Ultra-wideband radar methods and techniques of medical sensing and imaging. In Smart Medical and Biomedical Sensor Technology III (vol. 6007, pp. 96-107). SPIE. (Year: 2005).*

(Continued)

*Primary Examiner* — Keith M Raymond
*Assistant Examiner* — Johnathan Maynard
(74) *Attorney, Agent, or Firm* — CHRISTENSEN O'CONNOR JOHNSON KINDNESS PLLC (57) ABSTRACT

A micro impulse radar (MIR) system includes art MIR transceiver circuit configured to transmit, towards a subject, at least one transmitted radar signal, and receive at least one radar return signal. The system includes a control circuit configured to generate a control signal defining a radar signal parameter of the at least one transmitted radar signal, provide the control signal to the MIR transceiver circuit to cause the MIR transceiver circuit to transmit the at least one transmitted signal based on the radar signal parameter, and
(Continued)

determine, based on the at least one radar return signal, a physiological parameter of the subject.

24 Claims, 5 Drawing Sheets

Related U.S. Application Data (60) Provisional application No. 62/813,620, filed on Mar. 4, 2019, provisional application No. 62/747,614, filed on Oct. 18, 2018.

(51) Int. Cl.
| | | |
|---|---|---|
| *A61B 5/0205* | (2006.01) | |
| *A61B 5/024* | (2006.01) | |
| *A61B 5/0285* | (2006.01) | |
| *A61B 5/029* | (2006.01) | |
| *A61B 5/08* | (2006.01) | |
| *G01S 7/40* | (2006.01) | |
| *G01S 13/00* | (2006.01) | |
| *G01S 13/88* | (2006.01) | |

(52) U.S. Cl.
CPC ............ *A61B 5/029* (2013.01); *A61B 5/6801* (2013.01); *G01S 7/40* (2013.01); *G01S 13/003* (2013.01); *G01S 13/88* (2013.01); *A61B 5/024* (2013.01); *A61B 5/0816* (2013.01)

(56) References Cited

U.S. PATENT DOCUMENTS

| | | | |
|---|---|---|---|
| 5,598,990 | A | 2/1997 | Farokhi |
| 6,024,119 | A | 2/2000 | Kirschner |
| 8,463,361 | B2 | 6/2013 | Tupin |
| 8,640,995 | B2 | 2/2014 | Corke |
| 11,701,020 | B2 * | 7/2023 | Hyde ................ G01S 13/003 600/407 |
| 2002/0125376 | A1 | 9/2002 | Karniadakis |
| 2004/0249257 | A1 | 12/2004 | Tupin |
| 2008/0128560 | A1 | 6/2008 | Hyde |
| 2011/0295102 | A1 | 12/2011 | Lakkis |
| 2012/0116202 | A1 | 5/2012 | Bangera et al. |
| 2014/0171749 | A1 * | 6/2014 | Chin ................ A61B 5/0015 600/300 |
| 2015/0257653 | A1 | 9/2015 | Hyde |
| 2016/0089052 | A1 | 3/2016 | Cho |
| 2016/0174842 | A1 | 6/2016 | Hyde |
| 2016/0213315 | A1 * | 7/2016 | Hyde .................... A61B 90/90 |
| 2016/0331255 | A1 * | 11/2016 | Cheatham, III ....... A61B 5/024 |
| 2017/0196761 | A1 * | 7/2017 | Hyde ............... A61M 16/0069 |

FOREIGN PATENT DOCUMENTS

| | | |
|---|---|---|
| WO | 02/103304 A2 | 12/2002 |
| WO | 2012/054086 A1 | 4/2012 |
| WO | 2016179405 A1 | 11/2016 |

OTHER PUBLICATIONS

Taylor, J. D. (2012). Medical Applications of Ultrawideband Radar. Ultrawideband Radar: Applications and Design, 285324. (Year: 2012).*
"Cardiosleeve". Print. 2018.
"Eko Electronic Stethoscope and Ekg—Telemedicine solutions". 2018, 8 pages https://www.ekohealth.com/telemedicine.
"Thinklabs One Digital Stethoscope" Thinklabs. 5 pages. 2018. https://store.thinklabs.com/products/thinklabs-one-digital-stethoscope.
Allison, "Qualcomm Smartwatch Chip May Include Eye-Tracking Support of AR Glasses", AR Wearable Tech News, May 14, 2008, 3 pages.
Azevedo and Mcewan, "Micropower Impulse Radar", Lawrence Livermore National Laboratory: Science and Technology Review, Jan. and Feb. 1996, pp. 17-29.
Batra et al., "Multiband Ofdm: Why It Wins for Uwb", EE Times, Jun. 24, 2003, 8 pages.
Cavagnaro et al., "UWB Pulse Propagation into Human Tissues", Physics in Medicine and Biology, 2013, vol. 58, pp. 1-10.
Chang, "Medical Device Development Efforts Using the Micropower Ultrawideband Impulse Radar (MUIR)", Lawrence Livermore Nation Security, LLC (2018).
Chiu et al., "Wearable Doppler Radar Health Monitor with gesture Control", Asia-Pacific Microwave Conference, Nov. 2014, pp. 944-946.
Fletcher and Kulkarni, "Wearable Doppler Radar with Integrated Antenna for Patient Vital Sign Monitoring", IEEE Radio and Wireless Symposium, Jan. 2010, pp. 276-279.
Hofland, "Heart rate and Respiratory Rate Detection Algorithm Based on the Kinect for Windows V2", University of Amsterdam, Jul. 7, 2016 pp. 1-21.
Impulse Geophysics. Impulse Radar. Aug. 9, 2017, 1 page, https ://www.impulsegeophysics.com/construction-analysis.
Lazaro et al., "Analysis of Vital Signs Monitoring using an IR-UWB Radar", Progress in Electromagnetics Research, Oct. 2011, vol. 100, pp. 265-284.
Levy et al., "Micropower Impulse Radar: A Novel Technology for Rapid, Real-Time Detection of Pneumothorax", Emerg . Med. Int., May 30, 2011, vol. 2011, pp. 1-5.
Li et al., "UWB Radar with Array Antennas for Human Respiration and Heartbeat Detection", Centric, Oct. 2013, pp. 18-23.
LifeWave Biomedical, Athletics, LifeWave Biomedical, Oct. 16, 2017, pp. 1-3, http://www.lifewavebiomed.com/Athletics.
Novelda "Easy-to-Use Single-Chip Uwb Radar from Novelda Provides a Scalable Sensor Development Platform ." Mar. 7, 2017, 2 pages https ://www.microwavejournal.com/articles/28002-novelda-launches-easv-to-use-sinale-chio-uwb-radar.
Novelda As. X4M05 Radar Sensor. Xethru . Aug. 25, 2017, pp. 1-5.
Obeid et al., "Doppler Radar for Heartbeat Rate and Heart Rate Variability Extraction", 3rd International Conference on E-Health and Bioengineering, Jan. 2011, pp. 1-4.
Pan, "Medical Applications of Ultra-Wideband", Survey Paper, 2007, pp. 1-12.
PVL Ltd . Radar Level Sensors. Aug. 9, 2017, pp. 1-6, http://www.pvl.co.uk/radar-level-sensors.html.
Qardio, Oct. 17, 2017, pp. 1-7, https://www.getqardio.com/qardiocore-wearable-ecg-ekg-monitoriphone/.
Satamoto et al., "Accurate Heartbeat Monitoring Using Ultra-wideband radar", IEICE Electronics Express, Jan. 28, 2015, vol. 12, No. 25, pp. 1-7.
Sensible Medical, Overview, Sensible Medical, Oct. 16, 2017, pp. 1-10, https ://www.impulsegeophysics.com/construction-analysis.
Steffen et al., "Mobile Noncontact Monitoring of Heart and Lung Activity", IEEE Transactions on Biomedical Circuits and Systems, Dec. 2007, vol. 1, No. 4, pp. 250-257.
Stull, "LANDMARC—Making Land-Mine Detection and Removal Practical", Science Technology Review, Nov. 1997, pp. 18-20.
Yong et al., "An Overview of Ultra-Wideband Technique Application for Medial Engineering" IEEE Conference Publication, May 23-27, 2007, pp. 408-411.
Yoon et al., "A Flexible and Wearable Human Stress Monitoring Patch", Nature: Scientific Reports, Mar. 23, 2016, vol. 6, pp. 1-11.
Zito et al., "Feasibility Study and Design of a Wearable System-on-a-Chip Pulse Radar for Contactless Cardiopulmonary Monitoring", International Journal of Telemedicine and Applications, Mar. 17, 2008, vol. 2008, pp. 1-10.
PCT International Search Report; International App. No. PCT/US2019/042832; Oct. 22, 2019; pp. 1-4.
Berlin , David A. , et al. "Agreement Of Bioreactance Cardiac Output Monitoring With Thermodilution During Hemorrhagic Shock And Resuscitation In Adult Swine." Critical care medicine 45.2 (2017): e195-e201.

(56) References Cited

OTHER PUBLICATIONS

S. Latif, D. Flores-Tapia, S. Pistorius, and L. Shafai. Microwave and Optical Technology Letters 56, No. 4 (2014): 808-813.
Christine N. Paulson et al., "Ultra-wideband Radar Methods and Techniques of Medical Sensing and Imaging", Smart Medical and Biomedical Sensor Technology III, Nov. 11, 2005, 12 pages, Proc. of SPIE vol. 6007, 60070L.
Chinese Office Action mailed Apr. 1, 2024, issued in related Chinese Application No. 201980075839.2 filed Oct. 18, 2019, 29 pages.

\* cited by examiner

SYSTEM AND METHODS FOR MICRO IMPULSE RADAR DETECTION OF PHYSIOLOGICAL INFORMATION

CROSS-REFERENCE TO RELATED APPLICATIONS

This application is a continuation of application Ser. No. 16/657,688, filed Oct. 18, 2019, which claims the benefit of and priority to U.S. Provisional Application No. 62/747,614, filed Oct. 18, 2018, and U.S. Provisional Application No. 62/813,620; filed Mar. 4, 2019, the entire disclosures of which are hereby incorporated by reference herein for all purposes.

BACKGROUND

The present disclosure relates generally to the field of radar. More particularly, the present disclosure relates to systems and methods for radar detection of physiological information.

Radar systems can output signals that can be used to detect information regarding various subjects, including human subjects. Micro impulse radar (MIR) systems can output wideband signals that have relatively low power requirements. MIR systems can be relatively inexpensive to manufacture, as compared to existing radar systems.

SUMMARY

At least one embodiment relates to micro impulse radar (MIR) system. The system includes an MIR transceiver circuit configured to transmit, towards a subject, at least one transmitted radar signal; and receive at least one radar return signal. The system includes a control circuit configured to generate a control signal defining a radar signal parameter of the at least one transmitted radar signal; provide the control signal to the MIR transceiver circuit to cause the MIR transceiver circuit to transmit the at least one transmitted signal based on the radar signal parameter; and determine, based on the at least one radar return signal, a physiological parameter of the subject.

Another embodiment relates to a method. The method includes generating, by a control circuit, a control signal defining a radar signal parameter of a transmitted radar signal; providing, by the control circuit, the control signal to an MIR transceiver circuit; transmitting, by the MIR transceiver circuit, the transmitted radar signal based on the radar signal parameter; receiving, by the MIR transceiver circuit, a radar return signal; and determining, by the control circuit based on the radar return signal, a physiological parameter of a subject.

Another embodiment relates to a system. The system includes a micro impulse radar (MIR) sensor configured to receive a plurality of radar returns corresponding to an MIR radar signal transmitted towards a subject; and a control circuit configured to calculate a physiological parameter of the subject based on the plurality of radar returns.

Another embodiment relates to a method. The method includes receiving, by a micro impulse radar (MIR) sensor, a plurality of radar returns corresponding to an MIR radar signal transmitted towards a subject; and calculating, by a control circuit, a physiological parameter of the subject based on the plurality of radar returns.

Another embodiment relates to a system. The system includes a housing configured to be coupled to a subject; a sensor mounted in the housing, the sensor configured to detect information regarding the subject; and a control circuit coupled to the sensor, the control circuit configured to calculate a physiological parameter regarding the subject based on the information detected by the sensor.

Another embodiment relates to a method. The method includes detecting, by a sensor mounted in a housing coupled to a subject, information regarding the subject; and calculating, by a control circuit coupled to the sensor, a physiological parameter regarding the subject based on the information detected by the sensor.

This summary is illustrative only and is not intended to be in any way limiting.

BRIEF DESCRIPTION OF THE DRAWINGS

The disclosure will become more fully understood from the following detailed description, taken in conjunction with the accompanying figures, wherein like reference numerals refer to like elements, in which.

DETAILED DESCRIPTION

Before turning to the figures, which illustrate certain exemplary embodiments in detail, it should be understood that the present disclosure is not limited to the details or methodology set forth in the description or illustrated in the figures. It should also be understood that the terminology used herein is for the purpose of description only and should not be regarded as limiting.

Systems and Methods of Radar Detection of Physiological Information

Figure 1:
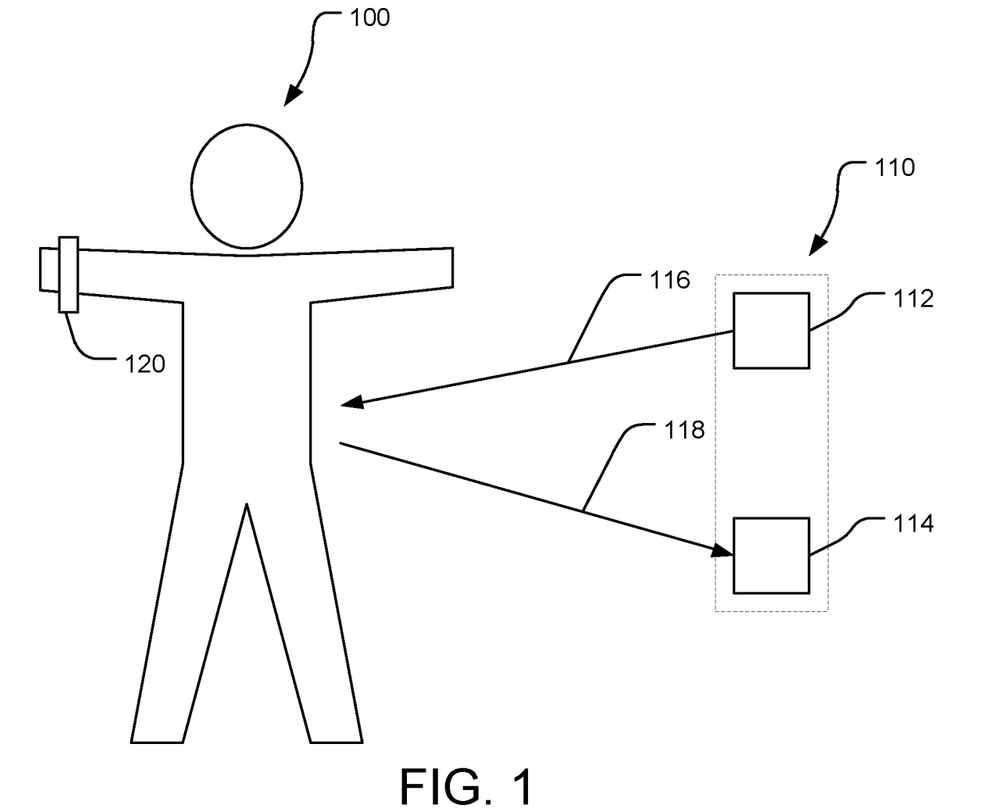
FIG. 1 is a schematic diagram of an MIR system in accordance with embodiment of the present disclosure.
Figure 2:
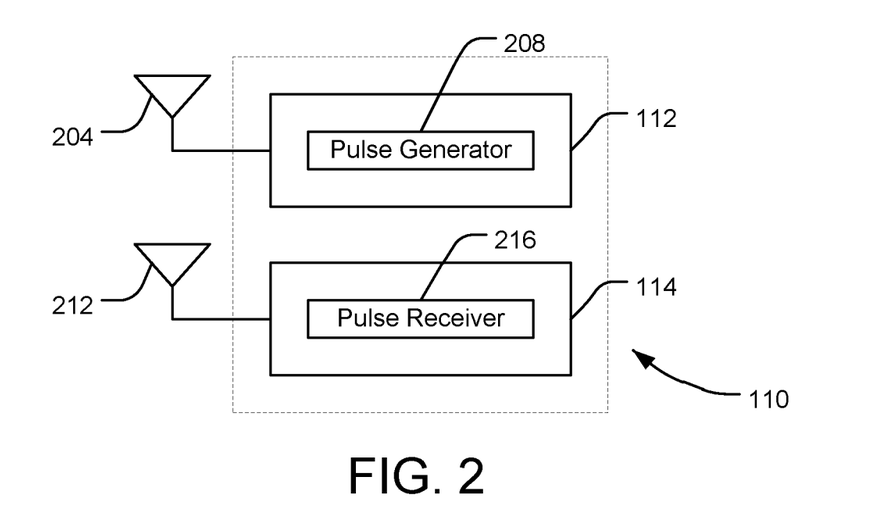
FIG. 2 is a schematic diagram of a transceiver of the MIR system of FIG. 1.

Referring now to FIGS. 1-2, a radar system 110 is shown according to an embodiment of the present disclosure. The radar system 110 is used to detect physiological information regarding a subject 100. The subject 100 may be a living subject, such as a mammalian (e.g., human) subject.

The radar system 110 includes a transmitter circuit 112 and a receiver circuit 114. The transmitter circuit 112 can transmit a first radar signal 116, such as in a direction towards the subject 100. For example, the transmitter circuit 112 can include a pulse generator 208 that applies a voltage to a transmit antenna 204 to cause the transmit antenna 204 to output the first radar signal 116. The transmitter circuit 112 can generate the first radar signal 116 to be an MIR signal. Various functions and systems described herein may be implemented using MIR signals as well as radar signals of other modalities and frequencies. The pulse generator 208 can apply the voltage in short pulses to generate MIR signals. For example, the pulses may have rise times on the order of picoseconds, and the pulse generator can generate the pulses on the order of millions of pulses per second. In some embodiments, a pulse width of the pulse outputted by the pulse generator is between approximately two hundred picoseconds and five nanoseconds. The pulse can be a relatively wideband pulse in terms of frequency, as compared to typical radar systems.

The receiver circuit 114 can include a receive antenna 212 (which may be co-located with/the same as the transmit antenna 204 of the transmitter circuit 112, or may be separate from the transmit antenna 204) and a pulse receiver 216. The receiver circuit 114 can receive a second radar signal 118 at the receive antenna 212, which can correspond to the first radar signal 116.

For example, the second radar signal 118 can be a radar return signal corresponding to the first radar signal 116. The second radar signal 118 can result from interaction of the first radar signal 116 and the subject 100. For example, the second radar signal 118 (e.g., return signal) can result from transmission, reflection, refraction, absorption (and later emission), shadowing, or otherwise scattering of the first radar signal 116 by the subject 100, or various combinations, such as multi-path combinations, thereof. Various signals may be described herein as first, second, third, or further numbered signals, which may refer to aspects of one or more signals at various points in space, time, output, or reception. In some embodiments, the receiver circuit 114 controls timing of reception of the second radar signal 118 so that a detection range of the receiver circuit 114 is relatively small. For example, the receiver circuit 114 can use an expected round-trip time of flight of the first radar signal 116 and the second radar signal 118 to maintain the detection range below a threshold detection range. In some embodiments, the threshold detection range is on the order of feet. In some embodiments, the threshold detection range is on the order of inches or less (e.g., for portable radar system 120). As such, the radar system 110 can maintain a relatively high signal to noise ratio by focusing on second radar signals 118 for which the radar system 110 can have a high confidence of corresponding to interaction of the first radar signals 116 with the subject 100. The pulse receiver 216 can receive the second radar signal 118 via the receive antenna 212 and generate an electronic signal (e.g., analog signal, radio frequency signal) corresponding to the second radar signal 118 for further analysis. The radar system 110 can receive and transmit the signals 116, 118 to detect a physiological parameter regarding the subject 100.

As shown in FIG. 1, a portable radar system 120 may be provided. The portable radar system 120 may be similar to the radar system 110, such as to output radar signals and receive return radar signals corresponding to the outputted radar signals. The portable radar system 120 may include straps, adhesives, or other attachment members to enable the portable radar system 120 to be worn by the subject 100.

Figure 3:
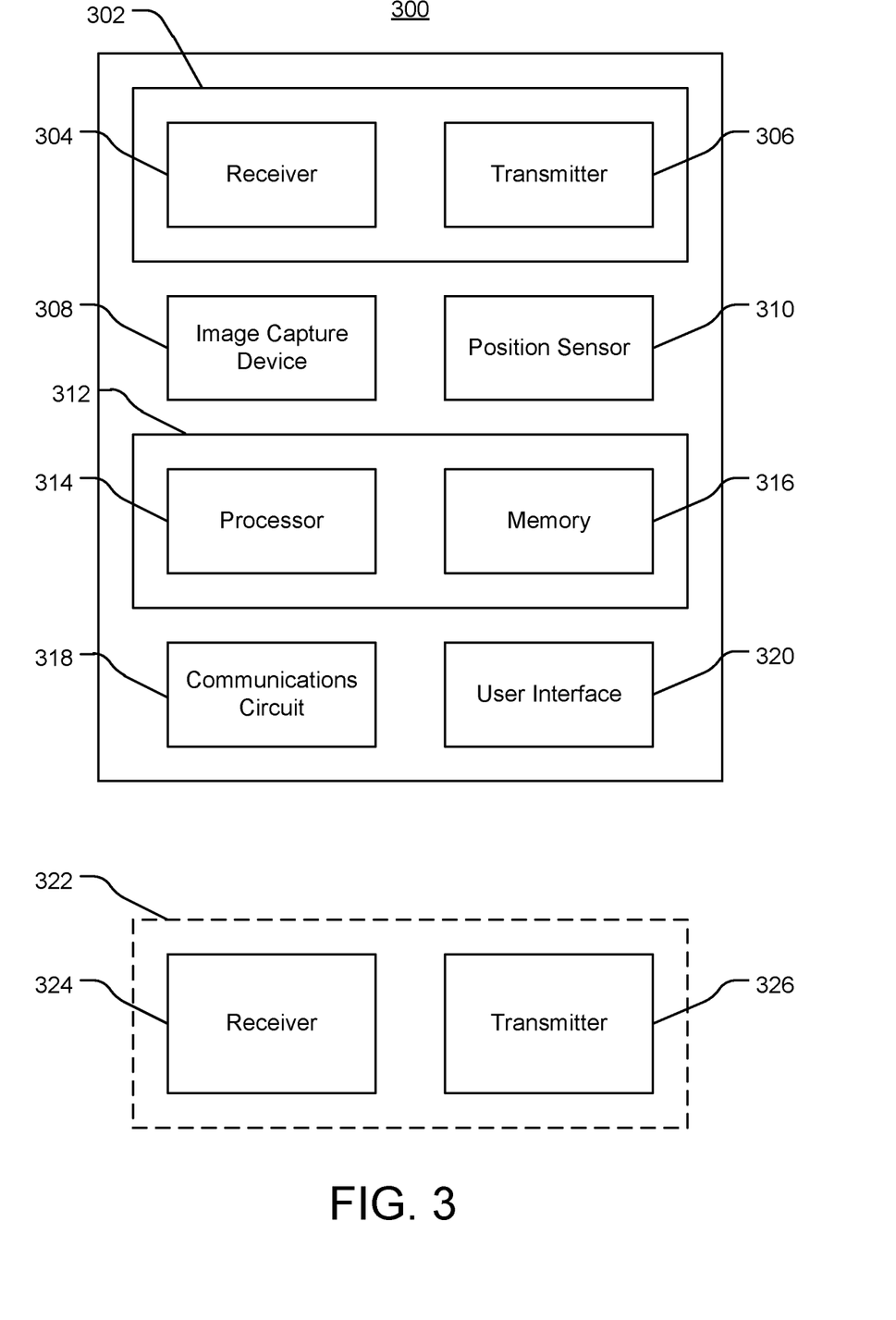
FIG. 3 is a block diagram of an MIR system in accordance with an embodiment of the present disclosure.
Figure 4:
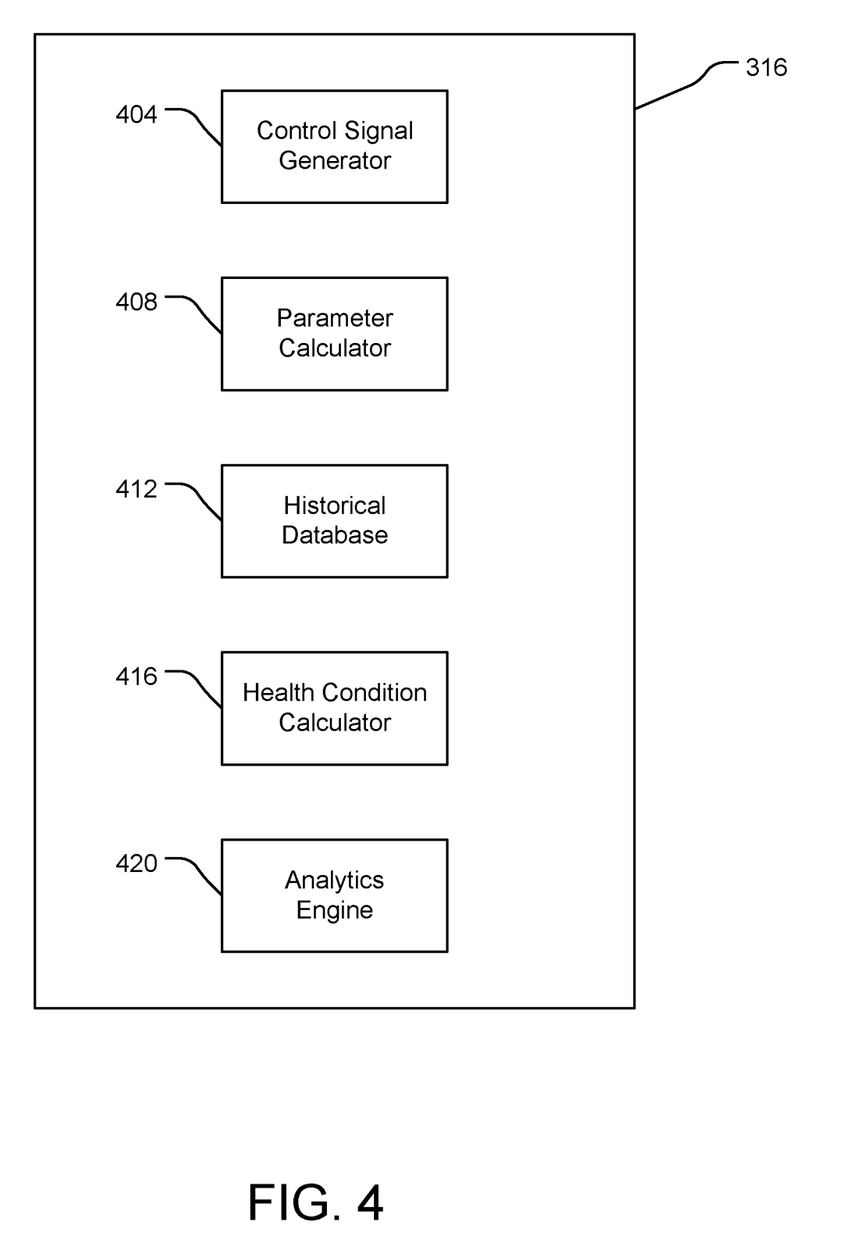
FIG. 4 is a block diagram of processing modules of the MIR system of FIG. 3.

Referring now to FIGS. 3-4, a radar system 300 is shown according to an embodiment of the present disclosure. The radar system 300 can incorporate features of the radar system 110, 120 described with reference to FIGS. 1-2.

The radar system 300 includes an MIR transceiver circuit 302 including an MIR transmitter 306 and an MIR receiver 304, and a processing circuit 312. The MIR transmitter 306 can incorporate features of the transmitter circuit 112 described with reference to FIGS. 1-2, and the MIR receiver 304 can incorporate features of the receiver circuit 114 described with reference to FIGS. 1-2. For example, the MIR transmitter 306 can transmit a first radar signal towards a subject, and the MIR receiver 304 can receive a second radar signal corresponding to the first radar signal.

The processing circuit 312 includes a processor 314 and memory 316. The processor 314 may be implemented as a specific purpose processor, an application specific integrated circuit (ASIC), one or more field programmable gate arrays (FPGAs), a system on a chip (SoC), a group of processing components (e.g., multicore processor), or other suitable electronic processing components. The memory 316 is one or more devices (e.g., RAM, ROM, flash memory, hard disk storage) for storing data and computer code for completing and facilitating the various user or client processes, layers, and modules described in the present disclosure. The memory 316 may be or include volatile memory or non-volatile memory and may include database components, object code components, script components, or any other type of information structure for supporting the various activities and information structures of the inventive concepts disclosed herein. The memory 316 is communicably connected to the processor 314 and includes computer code or instruction modules for executing one or more processes described herein. The memory 316 includes various circuits, software engines, and/or modules that cause the processor 314 to execute the systems and methods described herein.

As shown in FIG. 4, the memory 316 can include a control signal generator 404, a historical database 412, a parameter calculator 408, each of which the processor 314 can execute to perform the systems and methods described herein. The processing circuit 312 may be distributed across multiple devices. For example, a first portion of the processing circuit 312 that includes and executes the control signal generator 404 may be mechanically coupled to the transceiver circuit 302, while a second portion of the processing circuit 312 that includes an executes the parameter calculator 408, historical database 412, health condition calculator 416, and/or analytics engine 420 may be remote from the first portion and communicably coupled to the first portion (e.g., using communications circuit 318).

The radar system 300 can include an image capture device 308. The image capture device 308 can capture images regarding the subject 100, and provide the images to the processing circuit 312 (e.g., to h historical database 412).

The processing circuit 312 can execute object recognition and/or location estimation using the images captured by the image capture device 308. For example, the processing circuit 312 can extract, from a received image, features such as shapes, colors, edges, and/or spatial relationships between pixels of the received images. The processing circuit 312 can compare the extracted features to template features (e.g., a template of a human subject and recognize objects of the images based on the comparison, such as by determining a result of the comparison to satisfy a match condition. The template can include an expected shape of the subject 100. In some embodiments, the processing circuit 312 can estimate the location of anatomical features of the subject 100 based on the receive image, such as by estimating a location of a heart, lungs, or womb of the subject 100 based on having detected the subject 100.

The radar system 300 can include a position sensor 310. The position sensor 310 can detect a pose (e.g., at least one of a position or an orientation) of one or more components of the radar system 300. For example, the position sensor 310 can detect a pose of the MIR receiver 304 and detect a pose of the MIR transmitter 306. The position sensor 310 can include various sensors, such as accelerometers.

The radar system 300 can include a communications circuit 318. The communications circuit 318 can include wired or wireless interfaces (e.g., jacks, antennas, transmitters, receivers, transceivers, wire terminals, etc.) for conducting data communications with various systems, devices, or networks. For example, the communications circuit 318 can include an Ethernet card and port for sending and receiving data via an Ethernet-based communications network. The communications circuit 318 can include a WiFi transceiver for communicating via a wireless communications network. The communications circuit 318 can communicate via local area networks (e.g., a building LAN), wide area networks (e.g., the Internet, a cellular network), and/or conduct direct communications (e.g., NFC, Bluetooth). In some embodiments, the communications circuit 318 can conduct wired and/or wireless communications. For example, the communications circuit 318 can include one or more wireless transceivers (e.g., a Wi-Fi transceiver, a Bluetooth transceiver, a NFC transceiver, a cellular transceiver).

In some embodiments, the radar system 300 includes a user interface 320. The user interface 320 can receive user input and present information regarding operation of the radar system 300. The user interface 320 may include one or more user input devices, such as buttons, dials, sliders, or keys, to receive input from a user. The user interface 320 may include one or more display devices (e.g., OLED, LED, LCD, CRT displays), speakers, tactile feedback devices, or other output devices to provide information to a user.

Control Signal Generator

The control signal generator 404 controls operation of the MIR transceiver circuit 302. The control signal generator 404 can generate a control signal defining a radar signal parameter of the first radar signal to be transmitted by the MIR transmitter 306. The control signal generator 404 can define the radar signal parameter to include at least one of a frequency, an amplitude, a pulse width, or a pulse repetition frequency of the first radar signal.

In some embodiments, the control signal generator 404 defines the radar signal parameter based on an expected response of the subject to the first radar signal and/or an expected response of the first radar signal to the subject. For example, the control signal generator 404 can define the radar signal parameter based on an expected physical response that causes the second radar signal to have an expected signal to have an expected signal to noise ratio for a physiological parameter that the control signal generator 404 determines based on the second radar signal. The expected responses can correspond to factors such as whether the first radar signal will be, reflected by an outer surface of the subject 100 (e.g., including clothing worn by the subject), will penetrate the subject 100 before being absorbed or reflected, or a distance the first radar signal is expected to penetrate the subject 100. In some embodiments, the control signal generator 404 estimates the expected physical response based on biological and/or anatomical features of the subject 100, such as regions that the MIR transceiver circuit 302 targets that may be primarily composed of water molecules as compared to bone structures. For example, the control signal generator 404 can define the radar signal parameter so that the outputted first radar signals have a particular frequency, amplitude, pulse width, and/or pulse repetition frequency.

The control signal generator 404 can define the radar signal parameter by determining the expected response based on an actual signal to noise ratio of a prior received radar signal. For example, the control signal generator 404 can retrieve from the historical database 412 the actual signal to noise ratio of the prior received radar signal, a historical radar signal parameter corresponding to the prior received radar signal, and a parameter of the subject 100 corresponding to the prior received radar signal, and determine the expected response by comparing the data retrieved from the historical database 412 to corresponding data regarding operation of the radar system 300 to probe the subject 100. The parameter of the subject 100 may include a distance from the radar system 300 to the subject 100, or a location of a particular anatomical feature of the subject 100.

The control signal generator 404 can apply noise to the control signal, such as to randomize a pulse rate of the control signal. By applying noise to the control signal, the control signal generator 404 can uniquely encode the control signal, and thus the transmitted radar signal transmitted by the MIR transceiver circuit 302. In addition, applying noise can reduce the effect of interference from other electromagnetic radiation sources.

In some embodiments, the control signal generator 404 controls operation of the MIR receiver 304. For example, the control signal generator 404 can control a range gate of the MIR receiver 304. The range gate can correspond to an expected round trip time of the transmitted radar signal transmitted by the MIR transmitter 306 and the corresponding radar return signal received by the MIR receiver 304 based on interaction with the subject 100. For example, the control signal generator 404 can use a distance to the subject 100 to control the range gate. In some embodiments, the control signal generator 404 uses a location of a particular anatomical feature of the subject 100, such as the heart or lungs, to control the range gate.

Parameter Calculator

The parameter calculator 408 can determine, based on the second radar signal, a physiological parameter of the subject. For example, the parameter calculator 408 can calculate, based on the second radar signal, parameters such as locations of anatomical features, sizes of anatomical features, movement of anatomical features, movement of fluids (e.g., blood flow), or velocity data. The parameter calculator 408 can execute a Doppler algorithm to calculate velocity data. The parameter calculator 408 can calculate information such as an amplitude or power of the radar return signals at various frequencies, such as to generate a spectral analysis of the radar return signal. The parameter calculator 408 can calculate the physiological parameter to include at least one of a cardiac parameter, a pulmonary parameter, a blood flow parameter, or a fetal parameter based on the radar return signals. The parameter calculator 408 can calculate multiple parameters based on the radar return signal, such as by deconvolving the radar return signal. The radar return signal can include any of a variety of return signals including reflected, absorbed, refracted, or scattered signals, or combinations thereof, including multi-path signals.

In some embodiments, the parameter calculator 408 calculates the physiological parameter using at least one of a predetermined template or a parameter function. The predetermined template may include features such as expected signal amplitudes at certain frequencies, or pulse shapes of the radar return signal. The predetermined template may include anatomical features, such as shapes of vessel walls or cavity walls, such that the parameter calculator 408 can identify the movement of anatomical features (as well as blood flow and other fluid flow). The parameter function may be configured to convert data of the radar return signal (e.g., amplitude as a function of time at various frequencies) into various other variables, such as velocity or periodicity.

In some embodiments, the parameter calculator 408 calculates the physiological parameter based on an indication of a type of the physiological parameter. For example, the parameter calculator 408 can receive the indication based on user input. The parameter calculator 408 can determine the indication, such as by determining an expected anatomical feature of the subject 100 that the radar system 300 is probing using the transmitted radar signal. For example, the parameter calculator 408 can use image data from image capture device 308 to determine that the radar system 300 is probing a heart of the subject 100, and determine the type of the physiological parameter to be a cardiac parameter. The parameter calculator 408 can use the image data and the radar return signal to determine the type of the physiological parameter (e.g., to generate a candidate match between the radar return signal and the type of the physiological parameter and use the candidate match to adjust matching between the image data and template features representative of the expected anatomical feature). The parameter calculator 408 may use the determined type of the physiological parameter to select a particular predetermined template or parameter function to execute, or to increase a confidence that the radar return signal represents the type of physiological parameter (which may be useful for calculating the physiological parameter based on comparing the radar return signal to predetermined template(s) and searching for a match accordingly).

In some embodiments, the parameter calculator 408 calculates the cardiac parameter to include at least one of a heart volume, a heart rate, a heart stroke volume, a heart rate variation, a pulse shape, a heart pumping efficiency, or a cycle-to-cycle variation. For example, the parameter calculator 408 can extract a periodicity from the radar return signal to calculate the heart rate, and can monitor the periodicity across various cycles to calculate the heart rate variation. The parameter calculator 408 can use one or more pulse shape templates to calculate the pulse shape represented by the radar return signal. The parameter calculator 408 can monitor for changes in amplitude of the radar return signal at various frequencies to calculate the cycle-to-cycle variation. The cardiac parameter determined by the parameter calculator 408 can be used as a fingerprint (e.g., unique identifier) regarding the subject 100, which can be maintained in a database of the system 300 or outputted to remote devices.

The parameter calculator 408 can calculate the pulmonary parameter to include at least one of a breathing rate, a breathing rate variation, a volume in a chest of the subject 100, a volume change in the chest of the subject, or an air exchange efficiency. The parameter calculator 408 can determine the breathing rate based on a periodicity extracted from the radar return signal, including a periodic movement of walls of the lungs (e.g., determined using a shape template corresponding to the walls of the lungs). The parameter calculator 408 can determine the breathing rate variation by monitoring the breathing rate over several cycles. The parameter calculator 408 can determine the volume in the chest by determining the locations and/or shapes of walls of the lungs, and the volume change in the chest based on the volume and the periodic movement of the walls of the lungs. The parameter calculator 408 can calculate the air exchange efficiency (e.g., gas exchange efficiency) by monitoring parameters that may be associated with gas exchange, such as ventilation and/or perfusion parameters.

In some embodiments, the parameter calculator 408 calculates the fetal parameter to include similar parameters as the cardiac and/or pulmonary parameters. The parameter calculator 408 can use predetermined templates and/or parameter functions that have different characteristics specific to the fetal parameters (e.g., based on an expectation that a fetal heart rate is faster than an adult heart rate). The parameter calculator 408 can calculate the fetal parameter to include similar parameters as used for fetal ultrasound, such as a volume of amniotic fluid, fetal position, gestational age, or birth defects.

Historical Database

The historical database 412 can maintain historical data regarding a plurality of subjects, radar signals received for each subject, physiological parameters calculated for each subject, and radar system operations—for example, radar signal parameters-corresponding to the physiological parameters calculated for each subject. For example, the historical database 412 can assign, to each subject, a plurality of data structures each including a radar signal parameter of a first radar signal transmitted to probe the subject, a second radar signal received in return, and a physiological parameter calculated based on the second radar signal. The historical database 412 can maintain indications of intended physiological features to be probed using the radar signals (e.g., heart, lungs) and/or types of the calculated physiological parameters (e.g., cardiac, pulmonary). The historical database 412 can assign to each subject various demographic data (e.g., age, sex, height, weight).

The historical database 412 can maintain various parameters calculated based on radar return signals. For example, the historical database 412 can maintain physiological parameters, signal to noise ratios, health conditions, and other parameters described herein that the processing circuit 312 calculates using the radar return signals. The processing circuit 312 can update the historical database 412 when additional radar return signals are received and analyzed. The historical database 412 may include identifiers associated with one or more subjects and corresponding known parameters regarding the one or more subjects, such as physiological parameters (e.g., cardiac parameters, pulmonary parameters, biometric parameters) or templates or reference points corresponding to the known parameters regarding the subjects. The processing circuit 312 can use the parameter calculator 408 to generate a parameter of the subject 100, and compare the parameter of the subject 100 to one or more known parameters maintained by the historical database 412 regarding the one or more subjects to identify the subject 100 (e.g., compare the parameter determined by the parameter calculator 408 to the known parameters to generate one or more match scores, evaluate the match score using a threshold, and determine a selected known parameter to match the parameter of the subject 100 responsive to the match score satisfying the threshold). As such, the processing circuit 312 can retrieve an identifier of the subject 100 based on matching the parameter determined by the parameter calculator 408 to the known parameters maintained in the historical database 412. The processing circuit 312 can use the identifier for personal identification of the subject 100 for various purposes, including but not limited to retrieving thresholds for generating alerts specific to the subject 100 or identifying the subject 100 for security or gate entry purposes.

Health Condition Calculator

In some embodiments, the radar system 300 includes the health condition calculator 416. The health condition calculator 416 can use the physiological parameters calculated by the parameter calculator 408 and/or the historical data maintained by the historical database 412 to calculate a likelihood of the subject 100 having a particular health condition. The health condition calculator 416 can calculate likelihoods associated with medical conditions, emotion conditions, physiological conditions, or other health conditions.

In some embodiments, the health condition calculator 416 predicts a likelihood of the subject 100 having the health condition by comparing the physiological parameter to at least one of (i) historical values of the physiological parameter associated with the subject (e.g., as maintained in the historical database 412) or (ii) a predetermined value of the physiological parameter associated with the medical condition (e.g., a predetermined value corresponding to a match condition as described below). For example, the health condition calculator 416 can calculate an average value over time of the physiological parameter to determine a normal value or range of values for the subject 100, and determine the likelihood of the subject 100 having the medical condition based on a difference between the physiological parameter and the average value.

The health condition calculator 416 can maintain a match condition associated with each health condition. The match condition can include one or more thresholds indicative of radar return data and/or physiological parameters that match the health condition. As an example, the health condition calculator 416 can determine a likelihood of the subject 100 having arrhythmia by comparing a heart rate of the subject 100 to at least one of a minimum heart rate threshold (e.g., a threshold below which the subject 100 is likely to have arrhythmia) or a maximum heart rate threshold (e.g., a threshold above which the subject 100 is likely to have arrhythmia), and output the likelihood of the subject having arrhythmia based on the comparison. The health condition calculator 416 can store the outputted likelihoods in the historical database 412.

In some embodiments, the health condition calculator 416 updates the match conditions based on external input. For example, the health condition calculator 416 can receive a user input indicating a health condition that the subject 100 has; the user input may also include an indication of a confidence level regarding the health condition. The health condition calculator 416 can adjust the match condition, such as by adjusting the one or more thresholds of the match condition, so that the match condition more accurately represents the information of the external input. In some embodiments, the health condition calculator 416 updates the match condition by providing the external input as training data to the analytics engine 420.

The health condition calculator 416 can determine the likelihood of the subject 100 having the medical condition based on data regarding a plurality of subjects. For example, the historical database 412 can maintain radar return data, physiological parameter data, and medical conditional data regarding a plurality of subjects (which the analytics engine 420 can use to generate richer and more accurate parameter models). The health condition calculator 416 can calculate a statistical measure of a physiological parameter (e.g., average value, median value) for the plurality of subjects, and calculate an indication of the physiological parameter of the subject 100 being abnormal and/or calculate a likelihood of the subject 100 having the medical condition based on the statistical measure. In some embodiments, the health condition calculator 416 determines a likelihood that the subject 100 has a condition, such as sepsis, using the cardiac parameter determined by the parameter calculator 408. For example, the health condition calculator 416 can monitor at least one of the heart volume or the pumping efficiency determined by the parameter calculator 408, compare the monitored parameter to a corresponding threshold (which may be a predetermined threshold or a threshold specific to the subject 100), and output a likelihood of the subject 100 having sepsis or another condition related to the cardiac parameter based on the comparison. The radar system 300 can generate an alert regarding the condition responsive to the likelihood of the subject 100 having the condition, which may be able to be generated before other indicators are able to detect the condition (e.g., the condition, such as sepsis, may be able to be detected before an EKG or other heart monitoring sensor outputs data indicative of the condition due to changes in blood volume pumped by the heart occurring before detectable changes in electrical activity of the heart).

Analytics Engine

In some embodiments, the radar system 300 includes an analytics engine 420. The analytics engine 420 can be used to calculate various parameters described herein, including where relatively large amounts of data may need to be analyzed to calculate parameters as well as the thresholds used to evaluate those parameters. For example, the parameter calculator 408 can execute the analytics engine 420 to determine the thresholds used to recognize physiological parameters. The health condition calculator 416 can execute the analytics engine 420 to determine the thresholds used to determine whether physiological parameters indicate that the subject 100 has a particular medical condition. In some embodiments, the parameter calculator 408 can execute the analytics engine 420 to calculate a plurality of parameters based on the second radar signal. For example, the analytics engine 420 can calculate each of a cardiac parameter and a pulmonary parameter based on the second radar signal. The analytics engine 420 can determine several parameters by deconvolving the second radar signal, as the second radar signal may represent a convolution of multiple parameters, such as heart rate, heart volume, heart contractions, and breathing rate. The analytics engine 420 may execute various algorithms to extract the plurality of parameters from the second radar signal, including machine learning algorithms described herein that may provide models of the parameters to be extracted. The analytics engine 420 can operate various models, engines, functions, filters, equations, algorithms, or combinations thereof to generate information based on sensor data acquired by the system 300.

In some embodiments, the analytics engine 420 includes a parameter model. The analytics engine 420 can use training data including input data and corresponding output parameters to train the parameter model by providing the input data as an input to the parameter model, causing the parameter model to calculate a model output based on the input data, comparing the model output to the output parameters of the training data, and modifying the parameter model to reduce a difference between the model output and the output parameters of the training data (e.g., until the difference is less than a nominal threshold). For example, the analytics engine 420 can execute an objective function (e.g., cost function) based on the model output and the output parameters of the training data.

The parameter model can include various machine learning models that the analytics engine 420 can train using training data and/or the historical database 412. The analytics engine 420 can execute supervised learning to train the parameter model. In some embodiments, the parameter model includes a classification model. In some embodiments, the parameter model includes a regression model. In some embodiments, the parameter mod& includes a support vector machine (SVM). In some embodiments, the parameter model includes a Markov decision process engine.

In some embodiments, the parameter model includes a neural network. The neural network can include a plurality of layers each including one or more nodes (e.g., neurons, perceptions), such as a first layer (e.g., an input layer), a second layer (e.g., an output layer), and one or more hidden layers. The neural network can include characteristics such weights and biases associated with computations that can be performed between nodes of layers, which the analytics engine 420 can modify to train the neural network. In some embodiments, the neural network includes a convolutional neural network (CNN). The analytics engine 420 can provide the input from the training data and/or historical database 412 in an image-based format (e.g., computed radar values mapped in spatial dimensions), which can improve performance of the CNN as compared to existing systems, such as by reducing computational requirements for achieving desired accuracy in calculating health conditions. The CNN can include one or more convolution layers, which can execute a convolution on values received from nodes of a preceding layer, such as to locally filter the values received from the nodes of the preceding layer. The CNN can include one or more pooling layers, which can be used to reduce a spatial size of the values received from the nodes of the preceding layer, such as by implementing a max pooling function, an average pooling function, or other pooling functions. The CNN can include one or more pooling layers between convolution layers. The CNN can include one or more fully connected layers, which may be similar to layers of neural networks by connecting every node in fully connected layer to every node in the preceding layer (as compared to nodes of the convolution layer(s), which are connected to less than all of the nodes of the preceding layer).

The analytics engine 420 can train the parameter model by providing input from the training data and/or historical database 412 as an input to the parameter model, causing the parameter model to generate model output using the input, modifying a characteristic of the parameter model using an objective function (e.g., loss function), such as to reduce a difference between the model output and the and the corresponding output of the training data. In some embodiments, the analytics engine 420 executes an optimization algorithm that can modify characteristics of the parameter model, such as weights or biases of the parameter model, to reduce the difference. The analytics engine 420 can execute the optimization algorithm until a convergence condition is achieved (e.g., a number of optimization iterations is completed; the difference is reduced to be less than a threshold difference).

As described further below, the analytics engine 420 can train the parameter model using input from multiple sensor modalities. By using input from multiple sensor modalities, such as MIR and electrocardiography to analyze cardiac parameters, the analytics engine 420 can more accurately train the parameter model and improve operation of the radar system 300, as the input from multiple sensor modalities represents multiple, independent sets of correlated data. For example, both the MIR data and electrocardiography data can be independently determined to represent cycle-to-cycle variation, increasing the accuracy of the parameter model when these independent data sets are correlated in training the parameter model.

Pose Control

In some embodiments, the radar system 300 generates instructions regarding adjusting the pose A at least one of the MIR receiver 304 or the MIR transmitter 306. The processing circuit 312 can receive an initial pose of the at least one of the MIR receiver 304 or the MIR transmitter 306 from the position sensor 310. The processing circuit 312 can receive, from the image capture, device 308, an image of the subject 100, and as described above, execute object recognition to detect the subject 100 in the image and estimate the location of anatomical features of the subject 100 (e.g., estimate the heart to be in a particular location). As such, the processing circuit 312 can generate instructions for adjusting the initial pose of the at least one of the MIR receiver 304 or the MIR transmitter 306 using the detection of the subject 100, such as to move the MIR receiver 304 and/or the MIR transmitter 306 closer to or further from the subject 100, or to adjust an angle at which the MIR transmitter 306 transmits the transmitted radar signals towards the subject 100 or the MIR receiver 304 receives the radar return signals from the subject 100. For example, the processing circuit 312 can generate instructions to orient the MIR receiver 304 to be pointed directly at the estimated location of the heart of the subject 100 to enable the processing circuit 312 to more effectively calculate cardiac parameters.

In some embodiments, the processing circuit 312 presents the instructions using the user interface 320. As such, a user can use the instructions to determine how to adjust the pose of the at least one of the MIR receiver 304 or the MIR transmitter 306 based on the instructions. The processing circuit 312 can iteratively evaluate the pose of the at least one of the MIR receiver 304 or the MIR transmitter 306, and update the presented instructions as the pose is adjusted. In some embodiments, the radar system 300 includes an actuator coupled to the at least one of the MIR receiver 304 or the MIR transmitter 306, and the processing circuit 312 can cause the actuator to automatically adjust the pose.

In some embodiments, the MIR transceiver circuit 302 includes an electronically scanned array (ESA), such as to selectively direct the transmitted radar signals in particular directions. The processing circuit 312 can generate instructions, in a similar manner as for adjusting the pose, to control operation of the ESA to steer the transmitted radar signals transmitted by the ESA.

Tomography

The processing circuit 312 can control operation of the MIR transceiver circuit 302 to execute MIR tomography. For example, the control signal generator 404 can generate instruct ions so that the MIR transmitter 306 can scan a plurality of sections of the subject 100, such as particular two-dimensional slices of interest. As described above, the processing circuit 312 can generate the instructions to indicate a desired change in pose of the MIR receiver 304 and/or the MIR transmitter 306, or to electronically steer the MIR transmitter 306, enabling the MIR transceiver circuit 302 to selectively scan particular sections of the subject 100.

Multiple Transmitters and/or Receivers

Referring further to FIG. 3, in some embodiments, the radar system 300 includes one or more remote MIR receivers 324 and/or one or more remote MIR transmitters 326, such as to enable bistatic and multistatic implementations. For example, the radar system 300 may include multiple transmitters (MIR transmitter 306 and one or more MIR transmitters 326); the radar system 300 may include multiple receivers (MIR receiver 304 and one or more MIR receivers 324). The remote MIR receivers 324 may be similar to the MIR receiver 324, and the remote MIR transmitters 326 may be similar to the MIR transmitter 306. The MIR transmitter 306 or the remote MIR transmitter 326 may be used to transmit the first radar signal, and multiple receivers 304, 324 may receive second radar signals corresponding to the first radar signal. For example, the MIR transmitters 306, 326 can transmit a first radar signal, the receiver 304 can receive a second radar signal corresponding to the first radar signal (which may include components from any of transmission, reflection, refraction, absorption (and later emission), shadowing, or otherwise scattering of the first radar signal by the subject 100), and the receiver 324 can receive a third radar signal (which may include components from any of transmission, reflection, refraction, absorption (and later emission), shadowing, or otherwise scattering of the first radar signal by the subject 100). The MIR transmitter 306 and the remote MIR transmitter 326 may be used to each transmit first radar signals (or respective first and second radar signals), and one or more of the receivers 304, 324 may receive second or third radar signal(s) corresponding to the first radar signals. Where multiple transmitters 306, 326 or receivers 304, 324 are used, various transmitters and receivers may be collocated (e.g., implemented using the same device) or separated from one another. In some embodiments, the transmitters) and receiver(s) may be positioned in particular locations that enable effective data capture and parameter determination, such as to avoid the radar signals passing through areas of the subject 100 that may attenuate the radar signals (e.g., at certain frequencies, water content of the subject 100 may attenuate the radar signals). For example, the MIR transmitter 306 can be positioned on a sternum region of the subject 100, and the MIR receiver 304 can be positioned on a spinal cord region of the subject 100, which can facilitate effective detection of parameters associated with the heart or lungs of the patient. In addition to the MIR receiver 304, the remote MIR receiver 324 may be positioned on an armpit region of the subject 100.

In some embodiments, the remote MIR receiver 324 and remote MIR transmitter 326 may be provided in a same transceiver 322, or may be remotely located from one another. The processing circuit 312 may receive pose data regarding each remote MIR receiver 324 and each remote MIR transmitter 326.

The processing circuit 312 can generate radar signal parameters for the one or more remote MIR transmitters 326 based on the radar signal parameter generated for the MIR transmitter 306. For example, the processing circuit 312 can generate the radar signal parameter for the remote MIR transmitter 326 to have a different pulse width or pulse repetition frequency than the radar signal parameter for the MIR transmitter 306. The processing circuit 312 can encode a different noise on the control signal provided to the remote MIR transmitter 326 than to the MIR transmitter 306, to enable the MIR receivers 304, 324 to more effectively distinguish respective radar return signals.

The processing circuit 312 can combine radar return signals received from the MIR receiver 304 and the one or more MIR receivers 324 to generate a composite impression of the subject 100. In some embodiments, the processing circuit 312 uses the pose data regarding the MIR receivers 304, 324 and/or the MIR transmitters 306, 326 to combine the radar return signals. For example, the pose data, and a relationship of the pose data to the subject 100, can indicate different regions of the subject 100 that are probed using the transmitted radar return signals similarly, the pose data can indicate expected regions of the subject 100 that would be represented by the radar return signals.

Portable Radar Systems

Figure 5:
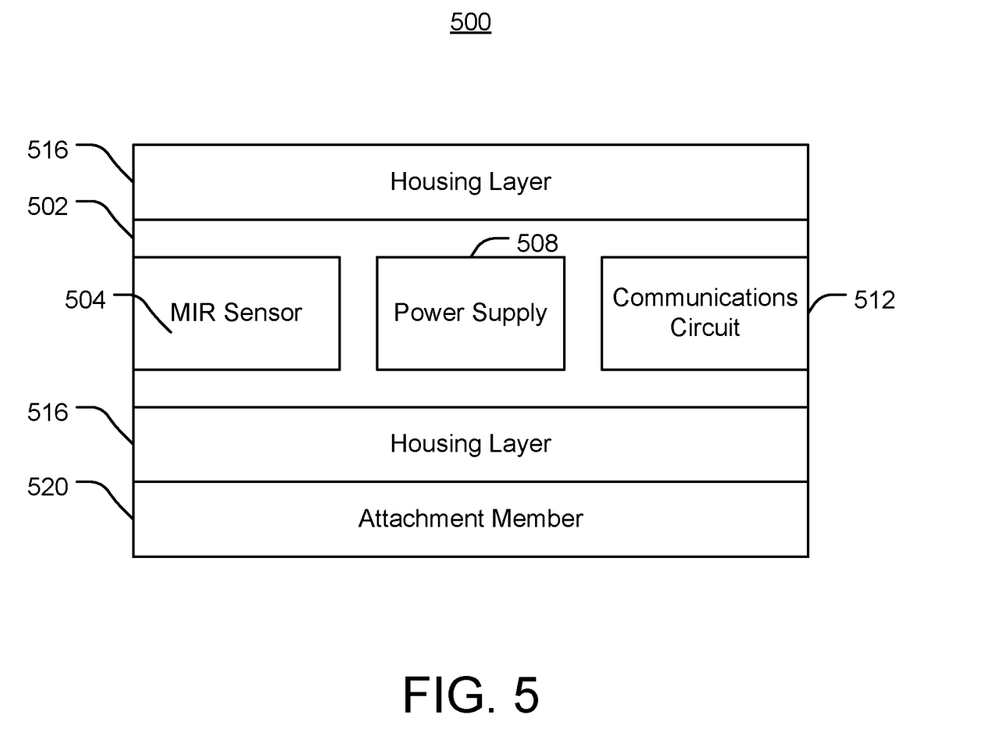
FIG. 5 is a schematic diagram of a portable MIR system in accordance with an embodiment of the present disclosure.

Referring now to FIG. 5, a portable radar system 500 is shown according to an embodiment of the present disclosure. The portable radar system 500 can incorporate features of the portable radar system 120 described with reference to FIG. 1. The portable radar system 500 can be a wearable device.

As shown in FIG. 5, the portable radar system 500 includes a sensor layer 502 including an MIR sensor 504 coupled to a power supply 508 and a communications circuit 512. The MIR sensor 504 can incorporate features of the MIR transceiver circuit 302 to transmit transmitted radar signals and receive radar return signals. The communications circuit 512 can incorporate features of the communications circuit 318 described with reference to FIG. 3. In some embodiments, the communications circuit 318 uses a relatively low power communications protocol, such as Bluetooth low energy.

The power supply 508 can have a relatively low capacity, given the relatively low power requirements of the MIR sensor 504 (e.g., less than 0.1 Watt). Similarly, the portable radar system 500 can be safe for continuous wear and usage, due to the relatively low power of the transmitted pulses (e.g., on the order of tens of microWatts).

The MIR sensor 504 can transmit sensor data using the communications circuit 512 to a remote device. In some embodiments, the MIR sensor 504 transmits the sensor data to a portable electronic device (e.g., cell phone), which can perform functions of the radar system 300, such as calculating physiological parameters based on the sensor data. As such, the portable radar system 500 can have relatively low size, weight, power, and/or cost.

The portable radar system 500 includes a housing layer 516. The housing layer 516 can be shaped and configured to be worn by the subject 100. In some embodiments, the housing layer 516 forms part of clothing or worn equipment (e.g., sports equipment), such as shoulder pads, helmets, or shoes. In some embodiments, the housing layer 516 is transparent to MIR signals.

The portable radar system 500 can include an attachment member 520. The attachment member 520 can enable the portable radar system 500 to be attached to a wearer or a body of the wearer (e.g., body of the subject 100). For example, the attachment member 520 can include an adhesive, a strap, or other attachment components. By attaching the portable radar system 500 to the wearer, the portable radar system 500 can enable longitudinal evaluation of physiological parameters in a medically safe manner (due to the low power output of the MIR signals).

Figure 6:
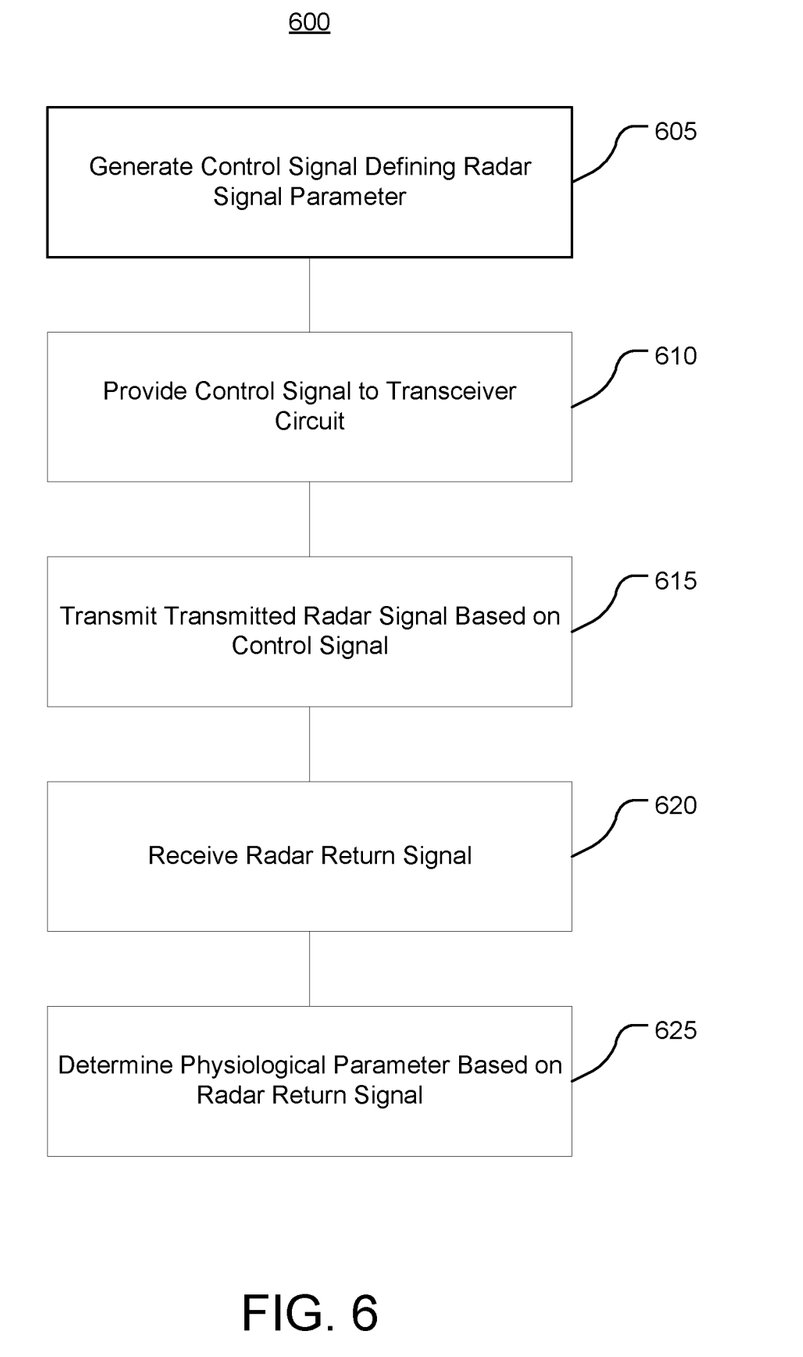
FIG. 6 is a flow diagram of a method of operating an MIR system in accordance with an embodiment of the present disclosure.

Referring now to FIG. 6, a method 600 of operating an MIR is shown according to an embodiment of the present disclosure. The method 600 can be performed using various systems described herein, including the radar system 110, the radar system 300, and the portable radar system 500.

At 605, a control signal defining a radar signal parameter of a transmitted (e.g., to be transmitted) radar signal by a control circuit. The control circuit can define the radar signal parameter based on an expected physical response of the subject to the transmitted radar signal that causes the radar return signal to have an expected signal to noise ratio for the physiological parameter. The control circuit can define the radar signal parameter to include at least one of a frequency, an amplitude, a pulse width, or a pulse repetition frequency of the transmitted radar signal. At 610, the control circuit provides the control signal to an MIR transceiver circuit.

At 615, the MIR transceiver circuit transmits the transmitted radar signal based on the control signal. For example, the MIR transceiver circuit can use an antenna to output the transmitted radar signal. The MIR transceiver circuit can transmit the transmitted radar signal towards a subject.

At 620, the MIR transceiver circuit receives a radar return signal. The radar return signal can correspond to the transmitted radar signal. For example, the radar return signal can be based on a reflection, refraction, absorption (and later emission), or other scattering of the transmitted radar signal because of interaction with the subject.

At 625, the control circuit determines a physiological parameter based on the radar return signal. The physiological parameter can include cardiac parameters, pulmonary parameters, gastrointestinal parameters, and fetal parameters. In some embodiments, the control circuit determines a likelihood of the subject having a medical condition based on the physiological parameter. The control circuit can control operation of the MIR transceiver circuit responsive to various conditions, such as a predetermined schedule (e.g., to periodically or continuously output MIR signal and receive return signals), user input, or detecting physiological parameters that meet a trigger threshold (e.g., if the control circuit detects that the heart rate variation meets a corresponding threshold, increase a rate of generating and receiving MIR signals to sample the heart rate variation more often).

As utilized herein, the terms "approximately," "about," "substantially", and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the disclosure as recited in the appended claims.

It should be noted that the term "exemplary" and variations thereof, as used herein to describe various embodiments, are intended to indicate that such embodiments are possible examples, representations, or illustrations of possible embodiments (and such terms are not intended to connote that such embodiments are necessarily extraordinary or superlative examples).

The term "coupled" and variations thereof, as used here in, means the joining of two members directly or indirectly to one another. Such joining may be stationary (e.g., permanent or fixed) or moveable (e.g., removable or releasable). Such joining may be achieved with the two members coupled directly to each other, with the two members coupled to each other using a separate intervening member and any additional intermediate members coupled with one another, or with the two members coupled to each other using an intervening member that is integrally formed as a single unitary body with one of the two members. If "coupled" or variations thereof are modified by an additional term (e.g., directly coupled), the generic definition of "coupled" provided above is modified by the plain language meaning of the additional term (e.g., "directly coupled" means the joining of two members without any separate intervening member), resulting in a narrower definition than the generic definition of "coupled" provided above. Such coupling may be mechanical, electrical, or fluidic.

The term "or," as used herein, is used in its inclusive sense (and not in its exclusive sense) so that when used to connect a list of elements, the term "or" means one, some, or all of the elements in the list. Conjunctive language such as the phrase "at least one of X, Y, and Z," unless specifically stated otherwise, is understood to convey that an element may be either X, Y, Z; X and Y; X and Z; Y and Z; or X, Y, and Z (i.e., any combination of X, Y, and Z). Thus, such conjunctive language is not generally intended to imply that certain embodiments require at least one of X, at least one of Y, and at least one of Z to each be present, unless otherwise indicated.

References herein to the positions of elements (e.g., "top," "bottom," "above," "below") are merely used to describe the orientation of various elements in the FIGURES. It should be noted that the orientation of various elements may differ according to other exemplary embodiments, and that such variations are intended to be encompassed by the present disclosure.

The hardware and data processing components used to implement the various processes, operations, illustrative logics logical blocks modules and circuits described in connection with the embodiments disclosed herein may be implemented or performed with a general purpose single- or multi-chip processor, a digital signal processor (DSP), an application specific integrated circuit (ASIC), a field programmable gate array (FPGA), or other programmable logic device, discrete gate or transistor logic, discrete hardware components, or any combination thereof designed to perform the functions described here in. A general purpose processor may be a microprocessor, or, any conventional processor, controller, microcontroller, or state machine. A processor also may be implemented as a combination of computing devices, such as a combination of a DSP and a microprocessor, a plurality of microprocessors, one or more microprocessors in conjunction with a DSP core, or any other such configuration, in some embodiments, particular processes and methods may be performed by circuitry that is specific to a given function. The memory (e.g., memory, memory unit, storage device) may include one or more devices (e.g., RAM, ROM, Flash memory, hard disk storage) for storing data and/or computer code for completing or facilitating the various processes, layers and modules described in the present disclosure. The memory may be or include volatile memory or non-volatile memory, and may include database components, object code components, script components, or any other type of information structure for supporting the various activities and information structures described in the present disclosure. According to an exemplary embodiment, the memory is communicably connected to the processor via a processing circuit and includes computer code for executing (e.g., by the processing circuit or the processor) the one or more processes described herein.

The present disclosure contemplates methods, systems and program products on any machine-readable media for accomplishing various operations. The embodiments of the present disclosure may be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. Combinations of the above are also included within the scope of machine-readable media. Machine-executable instructions include, for example, instructions and data which cause a general purpose computer, special purpose computer, or special purpose processing machines to perform a certain function or group of functions.

Although the figures and description may illustrate a specific order of method steps, the order of such steps may differ from what is depicted and described, unless specified differently above. Also, two or more steps may be performed concurrently or with partial concurrence, unless specified differently above. Such variation may depend, for example, on the software and hardware systems chosen and on designer choice. All such variations are within the scope of the dis closure. Likewise, software implementations of the described methods could be accomplished with standard programming techniques with rule-based logic and other logic to accomplish the various connection steps, processing steps, comparison steps, and decision steps.

It is important to note that e construction and arrangement of the MIR and stethoscope devices and systems as shown in the various exemplary embodiments is illustrative only. Additionally, any element disclosed in one embodiment may be incorporated or utilized with any other embodiment disclosed herein. Although only one example of an element from one embodiment that can be incorporated or utilized in another embodiment has been described above, it should be appreciated that other elements of the various embodiments may be incorporated or utilized with any of the other embodiments disclosed herein.

What is claimed is:

1. A wearable radar system, comprising:
    a transceiver circuit configured to:
        transmit, towards a subject, at least one transmitted radar signal having a radar signal parameter; and
        receive at least one radar return signal; and
    a control circuit configured to:
        retrieve an actual signal to noise ratio of a prior received radar return signal from a historical database;
        generate a control signal defining the radar signal parameter of the at least one transmitted radar signal, wherein the control circuit defines the radar signal parameter based on an expected response of the transmitted radar signal to a physiological parameter, and wherein the expected response is determined based on the actual signal to noise ratio of the prior received radar return signal;
        provide the control signal to the transceiver circuit to cause the transceiver circuit to transmit at least one transmitted signal having the radar signal parameter; and
        determine, based on a comparison of a signal to noise ratio of the at least one radar return signal and the actual signal to noise ratio of the prior received radar return signal from the historical database, the physiological parameter selected from a group comprising a heart rate variation, a heart volume, a heart stroke volume, a blood flow efficiency, a cardiac pulse shape, and a cardiac cycle-to-cycle variation.

2. The system of claim 1, wherein the radar signal parameter is at least one of a frequency, an amplitude, a pulse width, or a pulse repetition frequency of the transmitted radar signal.

3. The system of claim 1, comprising a transmitter configured to transmit an additional radar signal towards the subject, the transmitter spaced apart from the transceiver circuit.

4. The system of claim 1, comprising a receiver configured to receive at least one other radar return signal from the subject, the receiver spaced apart from the transceiver circuit, wherein the control circuit further determines the physiological parameter based on the at least one other radar return signal.

5. The system of claim 4, wherein the control circuit executes a tomography algorithm based on the radar return signal and the other radar return signal.

6. The system of claim 1, wherein the control circuit predicts a likelihood of the subject having a medical condition based on the physiological parameter.

7. The system of claim 6, comprising the historical database in which the control circuit maintains historical data regarding the physiological parameter, wherein the control circuit predicts the likelihood based on comparing the physiological parameter determined based on the radar return signal to the historical data.

8. The system of claim 7, wherein the control circuit maintains in the historical database, for each a plurality of subjects, an association between the physiological parameter and an indication of at least one medical condition, and predicts the likelihood of the subject having the at least one medical condition based on the association between the physiological parameter and the indication of at least one medical condition.

9. The system of claim 1, wherein the control circuit determines the physiological parameter based on a change in position of a cardiac tissue of the subject as a function of time.

10. The system of claim 1, wherein the control circuit is configured to calculate a signal to noise ratio and modify the radar signal parameter based on the signal to noise ratio.

11. The system of claim 1, wherein the control circuit is configured to analyse the at least one radar return signal to determine each of a first physiological parameter and a second physiological parameter.

12. The system of claim 1, further comprising at least one additional transmitter or at least one additional receiver to operate in a bistatic mode of operation or a multistatic mode of operation.

13. A method of operating a wearable radar device, comprising:
    retrieving, by a control circuit, an actual signal to noise ratio of a prior received radar return signal from a historical database;

generating, by the control circuit, a control signal defining a radar signal parameter of a transmitted radar signal, wherein generating the control signal comprises defining the radar signal parameter based on an expected response of the transmitted radar signal to a physiological parameter, and wherein the expected response is based on the actual signal to noise ratio of the prior received radar return signal;

providing, by the control circuit, the control signal to a transceiver circuit;

transmitting, by the transceiver circuit, the transmitted radar signal based on the radar signal parameter;

receiving, by the transceiver circuit, a radar return signal; and determining, by the control circuit based on a comparison of a signal to noise ratio of the radar return signal and the actual signal to noise ratio of the prior received radar return signal from the historical database, the physiological parameter selected from a group comprising a heart rate variation, a heart volume, a heart stroke volume, a blood flow efficiency, a cardiac pulse shape, and a cardiac cycle-to-cycle variation.

14. The method of claim 13, wherein the radar signal parameter is at least one of a frequency, an amplitude, a pulse width, or a pulse repetition frequency of the transmitted radar signal.

15. The method of claim 13, comprising:
transmitting, by a transmitter, an additional radar signal towards a subject, the transmitter spaced apart from the transceiver circuit.

16. The method of claim 13, further comprising:
receiving, by a receiver, another radar return signal from a subject, the receiver spaced apart from the transceiver circuit; and
determining the physiological parameter based on the other radar return signal.

17. The method of claim 16, further comprising:
executing a tomography algorithm based on the radar return signal and the other radar return signal.

18. The method of claim 13, further comprising:
predicting a likelihood of a subject having a medical condition based on the physiological parameter.

19. The method of claim 18, comprising:
maintaining, in the historical database, historical data regarding the physiological parameter; and
predicting the likelihood based on comparing the physiological parameter determined based on the radar return signal to the historical data.

20. The method of claim 19, comprising:
maintaining in the historical database, for each of a plurality of subjects, an association between the physiological parameter and an indication of at least one medical condition; and
predicting the likelihood of a given subject having the at least one medical condition based on the association between the physiological parameter and the indication of at least one medical condition.

21. The method of claim 13, comprising:
determining the physiological parameter based on a change in position of a cardiac tissue of a subject as a function of time.

22. The method of claim 13, further comprising analysing the radar return signal to determine each of a first physiological parameter and a second physiological parameter from the radar return signal.

23. The method of claim 13, further comprising operating in a bistatic mode of operation or a multistatic mode of operation by using at least one additional transmitter or at least one additional receiver.

24. A wearable radar system, comprising:
a transceiver circuit configured to:
transmit, towards a subject, at least one transmitted radar signal having a radar signal parameter; and
receive at least one radar return signal; and
a control circuit configured to:
retrieve an actual signal to noise ratio of a prior received radar return signal from a historical database;
generate a control signal defining the radar signal parameter of the at least one transmitted radar signal, wherein the control circuit defines the radar signal parameter based on the actual signal to noise ratio of the prior received radar return signal;
provide the control signal to the transceiver circuit to cause the transceiver circuit to transmit at least one transmitted signal having the radar signal parameter; and
determine, based on a comparison of a signal to noise ratio of the at least one radar return signal and the actual signal to noise ratio of the prior received radar return signal from the historical database, a physiological parameter selected from a group comprising a heart rate variation, a heart volume, a heart stroke volume, a blood flow efficiency, a cardiac pulse shape, and a cardiac cycle-to-cycle variation.

* * * * *

UNITED STATES PATENT AND TRADEMARK OFFICE
CERTIFICATE OF CORRECTION

| | |
|---|---|
| PATENT NO. | : 12,138,030 B2 |
| APPLICATION NO. | : 18/330165 |
| DATED | : November 12, 2024 |
| INVENTOR(S) | : Roderick A. Hyde et al. |

Page 1 of 1

It is certified that error appears in the above-identified patent and that said Letters Patent is hereby corrected as shown below:

On the Title Page

| Column | Line | |
|---|---|---|
| 2 | 1 | Item (57), under "Abstract", delete "art MIR" and insert -- an MIR -- |

Signed and Sealed this
Twenty-eighth Day of October, 2025

John A. Squires
*Director of the United States Patent and Trademark Office*